United States Patent [19]
Arnaud

[11] Patent Number: 5,932,197
[45] Date of Patent: Aug. 3, 1999

[54] COSMETIC COMPOSITIONS AND THEIR USE IN OBTAINING A GLOSSY FILM

[75] Inventor: Pascal Arnaud, Creteil, France

[73] Assignee: L'Oreal, Paris, France

[21] Appl. No.: 08/806,142

[22] Filed: Feb. 25, 1997

[30] Foreign Application Priority Data

Mar. 1, 1996 [FR] France .................. 96 02626

[51] Int. Cl.$^6$ .................. A61K 7/027
[52] U.S. Cl. .................. 424/64; 424/63; 424/70.1; 424/70.7; 424/70.11; 424/401
[58] Field of Search .................. 424/401, 63, 60, 424/64, 70.1, 70.7, 70.11, DIG. 5

[56] References Cited

U.S. PATENT DOCUMENTS

| | | | |
|---|---|---|---|
| 4,061,780 | 12/1977 | Yoshida et al. | 424/64 |
| 4,323,693 | 4/1982 | Scala | 424/59 |
| 5,085,855 | 2/1992 | Shore | 424/64 |
| 5,567,427 | 10/1996 | Papadakis | 424/401 |

FOREIGN PATENT DOCUMENTS

| | | |
|---|---|---|
| A-23 60306 | 7/1974 | Germany . |
| WO-A-93/ 19074 | 9/1993 | WIPO . |

*Primary Examiner*—Jyothsna Venkat
*Attorney, Agent, or Firm*—Finnegan, Henderson, Farabow, Garrett & Dunner, L.L.P.

[57] ABSTRACT

A composition, particularly a lipstick composition or a composition to be applied to the lips, comprising at least one aromatic ester and at least one polymer comprising a —[C(CH$_3$)$_2$—CH$_2$]— unit, wherein said composition obtains a glossy film and can also be used in other compositions to obtain a glossy film.

35 Claims, No Drawings

COSMETIC COMPOSITIONS AND THEIR USE IN OBTAINING A GLOSSY FILM

The present invention relates to a composition, in particular a cosmetic composition, capable of being applied on the skin and/or on the mucous membranes, and in particular on the lips of the face.

Lipstick compositions generally comprise fatty substances, such as oils and waxes, and pigments. They may make it possible to obtain a matte or glossy film, depending in particular on the nature and/or proportions of the various constituents.

Thus, it is known that a good dispersion of the pigments and/or fillers in the compositions makes it possible to improve the gloss of the film.

It is also known that it is possible to improve the quality of the gloss of a lipstick film, for example by increasing, in the composition, the proportion of fatty phase, in particular oily phase, with respect to the pigmentary phase.

Moreover, certain oily compounds make it possible to obtain appropriate gloss characteristics; this is the case, in particular, with compounds capable of reflecting light and having a high refractive index, such as certain oily fatty substances. Preference is given, among the latter, to those having a low penetrating or absorbing power with respect to the skin, such as oily polymers.

These compounds are particularly advantageous because they also make it possible to improve the persistence and the hold of the film. Indeed, it is known that the gloss of a film has a tendency to decrease with time, in particular because of the possible poor hold of the film on the substrate, its wearing away or its migration into the fine lines of the skin or alternatively its transfer to other substrates.

However, it has been found that the presence in the composition, of a high percentage of these oily polymers brings about a decline in the cosmetic properties of the composition. A decline in the slippery nature of the composition during application is thus found, resulting in a spreading on the skin, which is undesirable. An increase in the sticky nature of the composition is also found after application, resulting in a degree of discomfort on the lips, as well as an inappropriate aesthetic quality.

The aim of the present invention is to provide a composition which makes it possible to obtain a film having good gloss after application on the substrate, while retaining appropriate cosmetic properties.

A subject of the present invention is a composition comprising, in an oily phase, the combination of at least one aromatic ester with at least one polymer comprising a —[C(CH$_3$)$_2$—CH$_2$]— unit, the oily phase having a refractive index ranging from approximately 1.4750 to 1.5050.

Another subject is a composition comprising the combination of at least one aromatic ester with at least one polymer comprising a —[C(CH$_3$)$_2$—CH$_2$]— unit which makes it possible to obtain a film having a gloss ranging from approximately 200 to 600.

Another subject of the invention is the use of the combination of at least one aromatic ester with at least one polymer comprising a —[C(CH$_3$)$_2$—CH$_2$]— unit in or for obtaining a composition which makes it possible to obtain a glossy film.

A further subject of the invention is the use of the combination of at least one aromatic ester with at least one polymer comprising a —[C(CH$_3$)$_2$—CH$_2$]— unit in or for obtaining a composition comprising an oily phase having a refractive index ranging from approximately 1.4750 to 1.5050.

"Glossy film" is understood to mean, in the present description, a film exhibiting a measurement of gloss preferably of the order from 200 to 600, more preferably from 300 to 500. The method of measuring the gloss is described immediately before the examples.

The inventor has surprisingly found that the fact of incorporating at least one polymer comprising a —[C(CH$_3$)$_2$—CH$_2$]— unit in combination with at least one aromatic ester made possible a composition which exhibits in particular good cosmetic properties, such as appropriate slipperiness, spreading, hold and stickiness, with respect to the compositions of the prior art which comprise solely oily polymers.

Moreover, it has been found that the specific esters selected in the context of the present invention, namely aromatic esters, also make it possible to improve the gloss of the film, because of the fact that they also possess, in most cases, a high refractive index.

The composition according to the invention thus comprises at least one aromatic ester and at least one polymer comprising a —[C(CH$_3$)$_2$—CH$_2$]— unit, which can represent all or only part of the oily phase of the composition, the oily phase moreover having to have a refractive index ranging from approximately 1.4750 to 1.5050.

As is known according to the state of the art, the change in direction of a light beam passing from one medium to another is related to the refractive indices of each of the media.

The refractive index of the oily phase according to the invention preferably ranges from 1.4750 to 1.5050, measured at room temperature (20–25° C.), for example, using a refractometer. The refractive index of the oily phase according to the invention more preferably ranges from 1.4800 to 1.500.

Mention may be made, among the aromatic esters capable of being used in the context of the present invention, of, alone or as a mixture, monoesters and polyesters of acids possessing an aromatic group with saturated or unsaturated, linear or branched alcohols having from 8 to 30 carbon atoms. It is also possible to employ esters of fatty acids, for example having from 8 to 30 carbon atoms, with alcohols having an aromatic group.

Mention may be made, in particular of monoesters of benzoic acid and polyesters of trimellitic acid with saturated or unsaturated, linear or branched alcohols having from 8 to 24 carbon atoms.

Mention may in particular be made of alkyl benzoates in which the alkyl group contains from 12 to 15 carbon atoms, isostearyl or octyldodecyl benzoates or alternatively benzyl laurate.

The aromatic esters according to the invention are preferably provided in the form of an oily liquid, or optionally, in pasty form, at room temperature.

The polymers having a —[C(CH$_3$)$_2$—CH$_2$]— unit according to the invention are known under the CTFA name of polybutene or polyisobutene. They preferably have an average molecular weight ranging from 500 to 50,000, and more preferably from 800 to 10,000. They can thus be presented in a liquid or pasty form.

In the context of the invention, a single polymer or a mixture of these polymers may be used.

Mention may be made, among the commercial polymers which come within the scope of the invention, of INDOPOL H100, INDOPOL H300 and INDOPOL H1500, from the company Amoco, and PERMETHYL 104A from the company Presperse, Inc.

The nature and/or amounts of aromatic esters and/or of polymers comprising a —[C(CH$_3$)$_2$—CH$_2$]— unit can be selected by the person skilled in the art, on the basis of his or her general knowledge, so as to obtain an (ester+polymer) mixture with a measurable refractive index. In particular, the mixture is preferably provided in the form of a clear and liquid mixture, for example having a dynamic viscosity at 25° C. of from 3 to 6 Pa.s., measured with a Contraves TV rotary viscometer equipped with an "MS-r4" rotor at a speed of 60 Hz, and a refractive index ranging from approximately 1.4750 to 1.5050.

Thus, in a specific embodiment of the invention, the (ester+polymer) mixture constitutes all of the oily phase of the composition, indeed all of the fatty phase of the composition.

According to the invention, at least one aromatic ester can preferably comprise from 5 to 95% of the oily phase, more preferably from 8 to 90% by weight, relative to the total weight of the oily phase.

According to the invention, at least one polymer comprising a —[C(CH$_3$)$_2$—CH$_2$]— unit can preferably comprise from 5 to 95% of the oily phase, more preferably from 10 to 50% by weight, relative to the total weight of the oily phase.

The composition can be provided in the form of a cosmetic, pharmaceutical or hygienic composition. It principally finds an application as a composition to be applied on the skin or mucous membranes, and in particular, to be applied on the lips of the face, such as a lipstick or a lip care or a lip balm, or a composition to be applied on a lipstick film, in particular in order to increase the gloss of the film.

The composition can then be provided in the form of a stick or rod or in the form of a supple paste, the viscosity of which can be measured. In the case of a supple paste, the dynamic viscosity at 25° C. preferably ranges from 3 to 35 Pa.s., measured with a Contraves TV rotary viscometer equipped with a "MS-r4" rotor at a speed of 60 Hz.

The composition can further be provided in the form of a liquid phase, optionally thickened and/or gelled by conventional thickeners.

The composition according to the invention can also be used as a care or make-up product for the skin, nails, eyelashes, and/or hair, such as hair balm, gel or lotion, a gel or lotion for caring for the nails, a mascara or an eyeliner, or even a cream or gel for the skin or body.

Depending on the application envisaged, the composition according to the invention can additionally comprise the constituents commonly employed in the type of application envisaged. However, persons skilled in the art know how to choose these additional constituents, and/or their amount, so that the advantageous properties of the composition according to the invention are not, or not substantially, detrimentally affected by the envisaged addition.

Thus, the composition can comprise, in its oily phase, oils of vegetable, mineral, animal or synthetic origin, in particular silicone and/or fluorinated origin. Use is preferably made of oils having a high refractive index, in particular greater than 1.45, in order not to detrimentally affect the gloss of the film.

Mention may be made, among the oils which can be envisaged, of volatile oils and non-volatile oils, which can be hydrocarbon, silicone and/or fluorinated oils, which can be cyclic or linear and which can be alone or as a mixture.

Volatile oil is understood to mean, in the present description, any oil capable of evaporating on contact with the skin. Mention may be made, among volatile silicone oils, of cyclotetradimethylsiloxane, cyclopentadimethylsiloxane, cyclohexadimethylsiloxane and methylhexyldimethylsiloxane. Mention may be made, among volatile hydrocarbon oils, of isoparaffins. Mention may be made, among silicone oils, of polydimethylsiloxanes (PDMS) and alkyldimethicones, phenylated silicone oils, such as polyphenylmethylsiloxanes, or silicones modified by aliphatic and/or aromatic groups, which are optionally fluorinated, or by functional groups, such as hydroxyl, thiol and/or amine groups.

Mention may be made, among non-silicone oils, of liquid paraffin, liquid petrolatum, perhydrosqualene, arara oil, sweet almond oil, calphyllum oil, palm oil, castor oil, sesame oil, avocado oil, jojoba oil, olive oil or cereal germ oil; fatty acid esters; alcohols; acetylglycerides; or octanoates, decanoates or ricinoleates or alcohols or of polyalcohols.

The composition can additionally comprise other fatty substances of vegetable, mineral, animal or synthetic origin, in particular, silicone and/or fluorinated origin.

Use can thus be made of fatty acid triglycerides; glycerides; hydrogenated oils which are solid at 25° C.; lanolins; or fatty esters which are solid at 25° C. Mention may be made, among the waxes which can be envisaged, alone or as a mixture, of animal, vegetable, mineral and synthetic waxes, such as beeswax; carnauba, candelilla, ouricury or Japan wax or cork fibre or sugarcane waxes; paraffin or lignite waxes; microcrystalline waxes; ozokerites; polyethylene waxes and the waxes obtained by the Fischer-Tropsch synthesis; silicone waxes; or fluorinated waxes.

The constituents of the fatty phase can in particular be chosen in a way varied by the person skilled in the art in order to prepare a composition having the desired properties, for example, with respect to consistency or texture.

The composition preferably comprises from 0 to 90% by weight of fatty constituents, other than the aromatic esters and the polymers containing a —[C(CH$_3$)$_2$—CH$_2$]— unit.

Depending on the application envisaged, the composition can also comprise a particulate phase which can be present in a proportion preferably of from 0 to 25% by weight, more preferably from 0 to 10% by weight, and which can comprise pigments and/or pearlescent agents and/or fillers commonly used in cosmetic compositions. The nature and the amount of pigments and/or fillers will preferably be chosen judiciously be the person skilled in the art, in order not to cause an excessive decline in the gloss of the film. From this perspective, the amount of pigments will preferably be limited to 10% by weight with respect to the total weight of the composition and the amount of fillers will be limited to 5% by weight with respect to the total weight of the composition.

The pigments can thus be present in the composition in the proportion preferably of from 0 to 15% by weight of the final composition, more preferably from 0 to 10% by weight. They can be white or colored, inorganic and/or organic. Mention may be made, among inorganic pigments, of titanium, zirconium or cerium dioxides, as well as zinc, iron or chromium oxides or ferric blue. Mention may be made, among organic pigments, of carbon black and baryium, strontium, calcium and aluminium lakes.

The pearlescent agents can be present in the composition in a proportion preferably of from 0 to 20% by weight, more preferably from 0 to 10% by weight. Mention may be made, among the pearlescent agents which can be envisaged, of mica covered with titanium oxide, with iron oxide, with natural pigment or with bismuth oxychloride and colored titanium oxide-coated mica.

The fillers, which can be present in a proportion preferably of from 0 to 15% by weight, more preferably from 0 to 5% by weight, in the composition, can be inorganic or synthetic, lamellar or non-lamellar. Mention may be made of talc, mica, silica, kaolin, nylon and polyethylene powders, teflon, starch, natural mother-of-pearl, boron nitride, microspheres, such as Expancel (Nobel Industries) or polytrap (Dow Corning), and silicone resin microbeads (Tospearls from Toshiba, for example).

The composition can additionally comprise any additive conventionally used in the cosmetics filed, such as antioxidants, fragrances, essential oils, preservatives, cosmetic active principles, moisturizers, vitamins, essential fatty acids, sphingolipids, artificial tanning agents, such as DHA, sunscreening agents, surfactants, or fat-soluble polymers, in particular, hydrocarbons, such as polyalkylenes, polyacrylates and silicone polymers which are compatible with fatty substances.

The invention is further illustrated by the following examples, which are not intended to be limiting in any way.
Measurement of the gloss The gloss of the compositions according to the invention was measured using a conventional photogoniometer.

The compositions were maintained at a temperature of 25° C.; a film with a thickness of 60 microns was spread over a glass plate at 33° C.

The incident beam arrived on the plate at an angle of −30° with respect to the perpendicular. The specular reflection S was measured at +30° and the diffuse reflection D was measured at 0°, with respect to the perpendicular.

The gloss G was determined as being the ratio S/D.

EXAMPLE 1

The following composition was prepared:

|  | % by weight |
| --- | --- |
| polybutene (Indopol H1500 from Amoco) | 45% |
| $C_{12}$–$C_{15}$ alkyl benzoate (Finsolv TN from Finetex) | 33% |
| PVP/hexadecene copolymer | 22% |

The refractive index of the mixture of the three constituents was 1.4905.

The constituents were heated and mixed at 90° C. until a homogenous mixture was obtained.

After cooling, a clear and liquid composition was obtained which could be applied on a lipstick film in order to increase the gloss thereof.

EXAMPLE 2

A lip gloss having the following composition was prepared:

|  | % by weight |
| --- | --- |
| polybutene (Indopol H100; molecular weight 965) | 45% |
| tridecyl trimellitate (DUB TMTD from Stearinerie Dubois) | 20% |
| polyethylene wax | 10% |
| pearlescent agents | 4% |
| preservatives, antioxidants | q.s. |
| octyldodecanol | q.s. for 100% |

The refractive index of the oily phase comprising "polybutene+tridecyl trimellitate+octyidodecanol" was 1.4823.

The fatty substances were mixed and heated at 90° C. until a homogenous mixture was obtained. The other constituents were added and then the mixture was poured into appropriate molds.

A lip gloss was thus obtained which made it possible to obtain a film exhibiting good gloss as well as appropriate cosmetic characteristics.

EXAMPLE 3

A lipstick having the following composition was prepared:

|  | % by weight |
| --- | --- |
| polybutene (Indopol H1500; molecular weight 2160) | 15% |
| $C_{12}$–$C_{15}$ alkyl benzoate (Finsolv TN from Finetex) | 20% |
| tridecyl trimellitate (DUB TMTD from Stearinerie Dubois) | 15% |
| phenyltrimethicone (DC556) | 5% |
| diisostearyl malate | 7% |
| lanolin | 13% |
| pigments | 10% |
| preservatives, antioxidants | q.s. |
| waxes (polyethylene, candelilla, carnauba) | q.s. for 100% |

The refractive index of the oily phase comprising "polybutene+alkyl benzoates+tridecyl trimellitate+phenyltrimethicone+diisostearyl malate" was 1.4833.

The constituents were mixed and heated at 95° C. After homogenization and milling, the mixture was poured at 95° C. into appropriate molds.

A lipstick was obtained which exhibited good cosmetic properties and which made it possible to obtain a glossy film on the lips.

I claim:

1. A composition comprising, in an oily phase, a mixture comprising at least one aromatic ester and at least one polymer comprising a —[C(CH$_3$)$_2$—CH$_2$]— unit, wherein said oily phase has a refractive index ranging from approximately 1.4750 to approximately 1.5050, and further wherein said at least one polymer has an average molecular weight ranging from 500 to 50,000.

2. A composition according to claim 1, wherein said oily phase has a refractive index ranging from 1.4800 to 1.5000.

3. A composition according to claim 1, wherein said composition produces a film having a gloss ranging from approximately 200 to approximately 600, as measured by a conventional photogoniometer.

4. A composition according to claim 3, wherein said gloss ranges from 300 to 500, as measured by a conventional photogoniometer.

5. A composition according to claim 1, wherein said at least one aromatic ester is a monoester of an acid having an aromatic group with saturated or unsaturated, linear or branched alcohols having from 8 to 30 carbon atoms; a polyester of an acid having an aromatic group with saturated or unsaturated, linear or branched alcohols having from 8 to 30 carbon atoms; or an ester of a fatty acid having from 8 to 30 carbon atoms with alcohols having an aromatic group.

6. A composition according to claim 5, wherein said at least one aromatic ester is a monoester of benzoic acid or a polyester of trimellitic acid with saturated or unsaturated, linear or branched alcohols having from 8 to 24 carbon atoms.

7. A composition according to claim 5, wherein said at least one aromatic ester is an alkyl benzoate with an alkyl group having from 12 to 15 carbon atoms, an isostearyl benzoate, an octyldodecyl benzoate, or benzyl laurate.

8. A composition according to claim 1, wherein said at least one polymer comprising a —[C(CH$_3$)$_2$—CH$_2$]— unit is a liquid or a paste, and wherein, at room temperature, said at least one aromatic ester is an oily liquid or a paste.

9. A composition according to claim 1, wherein said average molecular weight ranges from 800 to 10,000.

10. A composition according to claim 1, wherein said mixture has a dynamic viscosity at 25° C. ranging from 3 to 6 Pa.s.

11. A composition according to claim 1, wherein said oily phase comprises at least one aromatic ester in an amount ranging from 5 to 95% by weight, relative to the total weight of said oily phase.

12. A composition according to claim 11, wherein said at least one aromatic ester is present in an amount ranging from 8 to 90% by weight, relative to the total weight of said oily phase.

13. A composition according to claim 1, wherein said oily phase comprises at least one polymer comprising a —[C(CH$_3$)$_2$—CH$_2$]— unit in an amount ranging from 5 to 95% by weight, relative to the total weight of said oily phase.

14. A composition according to claim 13, wherein said at least one polymer comprising a —[C(CH$_3$)$_2$—CH$_2$]— unit is present in an amount ranging from 10 to 50% by weight, relative to the total weight of said oily phase.

15. A composition according to claim 1, wherein said oily phase additionally comprises at least one oil, wherein said at least one oil comprises vegetable oil, mineral oil, animal oil or synthetic oil, said at least one oil having a refractive index greater than 1.45.

16. A composition according to claim 15, wherein said synthetic oils are selected from silicone oils and fluorinated oils.

17. A composition according to claim 1, wherein said mixture constitutes 100% of said oily phase.

18. A composition according to claim 1, wherein said composition additionally comprises at least one fatty substance, wherein said at least one fatty substance is a wax, gum, a pasty fatty substance of vegetable origin, a pasty fatty substance of mineral origin, a pasty fatty substance of animal origin, or a pasty fatty substance of synthetic origin.

19. A composition according to claim 18, wherein said pasty fatty substance of synthetic origin is at least one silicone pasty fatty substance or at least one fluorinated pasty fatty substance.

20. A composition according to claim 1, wherein said composition additionally comprises a particulate phase in an amount ranging from 0 to 25% by weight, relative to the total weight of said composition.

21. A composition according to claim 20, wherein said particulate phase is present in an amount ranging from 0 to 10% by weight, relative to the total weight of said composition.

22. A composition according to claim 20, wherein said particulate phase comprises at least one pigment in an amount ranging from 0 to 15% by weight, relative to the total weight of said composition.

23. A composition according to claim 20, wherein said particulate phase comprises at least one pearlescent agent in a concentration ranging from 0 to 20% by weight, relative to the total weight of said composition.

24. A composition according to claim 1, wherein said composition is in the form of a cosmetic composition, a pharmaceutical composition or a hygienic composition.

25. A composition according to claim 24, wherein said composition to be applied on the lips is in the form of a lipstick, lip care, or lip balm.

26. A composition according to claim 24, wherein said composition is in the form of a stick or a rod or in the form of a supple paste with a dynamic viscosity at 25° C. ranging from 3 to 35 Pa•s.

27. A composition according to claim 24, wherein said composition is in the form of a care product or a make-up product for the skin, nails, eyelashes or hair.

28. A composition according to claim 27, wherein said composition is in a hair balm, hair gel, hair lotion, nailcare gel, nailcare lotion, mascara, eyeliner, skin cream, or skin gel.

29. A composition according to claim 28, wherein said composition is in the form of a composition to be applied on the lips or a composition to be applied on a lipstick film.

30. A method for obtaining a composition that produces a glossy film, said method comprising the step of mixing, in an oily phase, at least one aromatic ester and at least one polymer comprising a —[C(CH$_3$)$_2$—CH$_2$]— unit, wherein said oily phase has a refractive index ranging from approximately 1.4750 to approximately 1.5050, and further wherein said at least one polymer has an average molecular weight ranging from 500 to 50,000.

31. A method according to claim 30, wherein said glossy film has a gloss ranging from approximately 200 to approximately 600, as measured by a conventional photogoniometer.

32. A method according to claim 31, wherein said gloss ranges from 300 to 500, as measured by a conventional photogoniometer.

33. A method according to claim 30, further comprising the step of including said composition in a cosmetic, pharmaceutical, or hygienic composition.

34. A method according to claim 33, wherein said composition is a lipstick, lip care, lip balm, a composition to be applied on a lipstick film, a skin care product, a nail care product, a haircare product, or an eye make-up product.

35. A method according to claim 34, wherein said haircare product is a hair balm, hair gel or hair lotion; said nailcare product is a nail gel or nail lotion; said skin care product is a skin cream or skin gel; and said eye make-up product is a mascara or eyeliner.

* * * * *